United States Patent
Bildhauer et al.

(10) Patent No.: US 11,357,418 B2
(45) Date of Patent: Jun. 14, 2022

(54) ESTABLISHING CHANGES IN A B0 FIELD FROM REFLECTED WAVES

(71) Applicant: Siemens Healthcare GmbH, Erlangen (DE)

(72) Inventors: Petra Bildhauer, Nuremberg (DE); Flavio Carinci, Erlangen (DE); Michael Köhler, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 811 days.

(21) Appl. No.: 16/171,932

(22) Filed: Oct. 26, 2018

(65) Prior Publication Data

US 2019/0125207 A1 May 2, 2019

(30) Foreign Application Priority Data

Oct. 27, 2017 (DE) .......................... 102017219313.1

(51) Int. Cl.
*A61B 5/00* (2006.01)
*A61B 5/055* (2006.01)
(Continued)

(52) U.S. Cl.
CPC ............ *A61B 5/055* (2013.01); *A61B 5/0816* (2013.01); *A61B 5/113* (2013.01); *G01R 33/243* (2013.01);
(Continued)

(58) Field of Classification Search
CPC ....... A61B 5/113; A61B 5/243; G01R 33/243; G01R 33/3415; G01R 33/36; G01R 33/56509; G01R 33/5676; G01R 33/56563
See application file for complete search history.

(56) References Cited

U.S. PATENT DOCUMENTS 9,138,162 B2   9/2015 Stemmer
9,354,289 B2   5/2016 Landschuetz et al.
2015/0309147 A1* 10/2015 Schmitter .......... G01R 33/5612
                                                                600/410
(Continued)

FOREIGN PATENT DOCUMENTS

DE   102014209488 A1   11/2015
DE   102014218901 B4   2/2017

OTHER PUBLICATIONS

German Office Action for German Application No. 10 2017 219 313.1 dated Mar. 18, 2020.
Marques, J. P., and R. Bowtell. "Evaluation of a new method to correct the effects of motion-induced B0-field variation during fMRI." Proceedings of the 13th meeting of the ISMRM, Miami Beach, Florida, USA. 2005. p. 510.
(Continued)

*Primary Examiner* — Joel F Brutus
(74) *Attorney, Agent, or Firm* — Lempia Summerfield Katz LLC

(57) ABSTRACT

A control device establishes a change in a main magnetic field expected for a respective time instant and based on the established expected change in the main magnetic field, correctively adjusts the main magnetic field and/or a nominal receive frequency of the RF receive coil and/or a transmit frequency for subsequent RF transmit pulses and/or takes the expected change in the main magnetic field into account in the evaluation of the received MR signals. At least for some of the RF transmit pulses, the control device acquires, via a sensor device, a portion of the respective radiofrequency wave supplied to the RF transmit coil. The controller extracts therefrom an oscillation corresponding to a respiratory motion of the patient and based on the variation with time of the extracted oscillation, establishes the change
(Continued)

in the main magnetic field expected for the respective time instant.

10 Claims, 5 Drawing Sheets

(51) Int. Cl.

| | | |
|---|---|---|
| *G01R 33/36* | (2006.01) |
| *G01R 33/24* | (2006.01) |
| *A61B 5/08* | (2006.01) |
| *A61B 5/113* | (2006.01) |
| *G01R 33/3415* | (2006.01) |
| *G01R 33/565* | (2006.01) |
| *G01R 33/567* | (2006.01) |

(52) U.S. Cl.
CPC ......... *G01R 33/3415* (2013.01); *G01R 33/36* (2013.01); *G01R 33/5676* (2013.01); *G01R 33/56509* (2013.01); *G01R 33/56563* (2013.01)

(56) References Cited

U.S. PATENT DOCUMENTS

2015/0335268 A1 11/2015 Biber
2016/0081588 A1 3/2016 Zeller

OTHER PUBLICATIONS

Duerst, Yolanda, et al. "Real-time feedback for spatiotemporal field stabilization in MR systems." Magnetic resonance in medicine 73.2 (2015): 884-893.

Vannesjo, S. Johanna, et al. "Retrospective correction of physiological field fluctuations in high-field brain MRI using concurrent field monitoring." Magnetic resonance in medicine 73.5 (2015): 1833-1843.

Wehkamp, Niklas et al. "Prediction of breathing related B0-field fluctuations via artificial neural networks trained on magnetic field monitoring data" Proc. Intl. Soc. Mag. Reson. Med.; vol. 25, 2017.

* cited by examiner

ESTABLISHING CHANGES IN A B0 FIELD FROM REFLECTED WAVES

This application claims the benefit of DE 10 2017 219 313.1, filed on Oct. 27, 2017, which is hereby incorporated by reference in its entirety.

BACKGROUND

The present embodiments relate to determining changes in a magnetic field from reflected waves.

During the examination of patients in magnetic resonance systems, the respiratory motion of the patient may have a disruptive effect on the imaging. This problem is addressed in the publications U.S. Pat. No. 9,354,289 B2, DE 102014218901 B4, and U.S. Pat. No. 9,138,162 B2, for example.

The disruption is caused not just by the respiratory motion as such, which may lead to a particular part of the patient being located at different places at different times (e.g., because the chest of the patient rises and falls with the respiratory motion). Rather, the respiratory motion affects the amplitude and/or the orientation of the main magnetic field and also of the radiofrequency field also outside of the patient region that is moving due to the respiration. The respiratory motion of the patient may even cause interference during imaging of the head of the patient, for example.

The changes in the main magnetic field and the changes in the resonant frequency (Larmor frequency) associated therewith are particularly critical. These changes can induce artifacts, which may also vary from measurement to measurement due to the fact that the respiratory motion of the patient is never consistently the same.

An application in which the cited effects are particularly critical is a dynamic gradient-echo-based measurement with administration of contrast agent. Measurements of the type are employed frequently (e.g., in breast imaging). However, the cited effects may also occur during other measurements and cause interference there.

In order to avoid these problems, it is known to conduct measurements in magnetic resonance systems using respiratory triggering. In this situation, the patient is, for example, requested to hold his or her breath for those times during which the measurement is taking place. There are also automated methods that establish the respiratory state of the patient via a separate measurement or a specially introduced sensor and perform the measurement only in certain respiratory phases. However, a disadvantageous aspect with these methods is that in general the measurement time is longer. The method often may not be used or may be used only with considerable difficulties when a contrast agent is administered to the patient. In addition, the targeted breath-holding imposes demands in terms of cooperation on the part of the patient and the patient's physical and mental disposition. This may be critical in many cases.

A further method includes using special k-space trajectories during the scan. For example, in a three-dimensional measurement during a Cartesian sampling of the k-space, the phase and slice encoding sequences may be arranged in a targeted manner in order to reduce artifacts. However, a complete elimination of the artifacts may not be achieved by this.

Other methods employ special measurement instruments (e.g., field cameras) in order to enable the changes in the main magnetic field to be quantified and then compensated for during the measurement. The compensation may be carried out during the sending of subsequent radiofrequency transmit pulses, during the reception of magnetic resonance signals, and during the evaluation of already received magnetic resonance signals.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a change in a main magnetic field expected due to a respiratory motion of a patient may be established in a simple and reliable way and may be taken into account during.

According to an embodiment, an operating method is embodied in that at least in the case of some radiofrequency transmit pulses, a control device acquires, via a sensor device, a portion of the respective radiofrequency wave supplied to the radiofrequency transmit coil. The portion is reflected by the radiofrequency transmit antenna. From the reflected portions of the radiofrequency waves, the control device extracts an oscillation corresponding to a respiratory motion of the patient, and the control device establishes the change in the main magnetic field expected for the respective time instant based on the variation with time of the extracted oscillation.

Within the scope of the present embodiments, the reflected portion is therefore acquired at a suitable point of the radiofrequency line between the power amplifier, which generates the radiofrequency wave and supplies the radiofrequency wave via the radiofrequency line to the radiofrequency transmit antenna, and the radiofrequency transmit antenna itself (e.g., within the hardwired path between the two components). This is possible in a simple manner and with minimal technical overhead. With minimal technical overhead (e.g., simply by a suitable filtering and smoothing function), the oscillation corresponding to the respiratory motion of the patient may be extracted. The subsequent determination of the expected change in the main magnetic field may then be accomplished in a simple manner by scaling.

For example, the reflected power from the reflected wave may be utilized for extracting the oscillation. If necessary, however, a different characteristic parameter such as, for example, the phase of the reflected wave or a voltage of the reflected wave may also be derived and made use of. In one embodiment, using the characteristic parameters, the oscillation may be determined, and from the determined oscillation, the expected change in the main magnetic field may be established.

In one embodiment, the control device determines the expected change in the main magnetic field based on the variation with time of the oscillation in conjunction with a function already predefined before the patient is arranged in the examination zone. The function places the expected change in the main magnetic field in relation to the current elongation of the oscillation. This approach has the advantage that the function is already determined in advance, so that the period of time during which the patient is required to remain in the examination zone of the magnetic resonance system may be minimized.

In order to determine the cited function, preliminary measurements may, for example, be carried out in advance using a plurality of test subjects. The function is then determined from the plurality of measurements. The determined function is then stored so that the determined function is available to the control device for establishing the expected change in the main magnetic field.

Alternatively, the control device may initially perform test measurements once the patient has been arranged in the examination zone. During the test measurements, the control device supplies a radiofrequency wave to the radiofrequency transmit coil in each case, such that a radiofrequency sample pulse is applied to the radiofrequency transmit coil in each case. In each case during the radiofrequency sample pulses a portion of the respective radiofrequency wave supplied to the radiofrequency transmit coil is acquired via the sensor. The portion is reflected by the radiofrequency transmit antenna. A measured variable that is different from the reflected portion and is characteristic of the change in the main magnetic field is additionally acquired by a further sensor device during the radiofrequency sample pulses. The change in the main magnetic field during the radiofrequency sample pulses is established based on the measured variable that is different from the reflected portion. Based on the portions reflected by the radiofrequency transmit antenna during the radiofrequency sample pulses and the established change in the main magnetic field, a function that places the expected change in the main magnetic field in relation to the current elongation of the oscillation is determined, and the expected change in the main magnetic field is established based on the variation with time of the oscillation in conjunction with the determined function.

This approach has the advantage that the function based on which the expected change in the main magnetic field is established is determined individually for the respective patient. It is therefore to be expected that the function delivers better results than a function based on a plurality of test subjects.

In the simplest case, it is assumed that the change in the main magnetic field is uniformly the same across the entire examination zone. Alternatively, the control device may establish the expected change in the main magnetic field within the examination zone in a spatially resolved manner.

According to one or more of the present embodiments, the processing of the machine code by the control device causes the control device to operate the magnetic resonance system in accordance with an embodiment of the operating method.

According to one or more of the present embodiments, the control device is programmed with an embodiment of a computer program such that the control device operates the magnetic resonance system in accordance with an embodiment of the operating method.

According to one or more of the present embodiments, a magnetic resonance system includes a sensor device for acquiring a portion of the respective radiofrequency wave supplied to the radiofrequency transmit coil. The portion is reflected by the radiofrequency transmit antenna at least in the case of some of the radiofrequency transmit pulses. In addition, the magnetic resonance system includes the control device according to an embodiment.

DETAILED DESCRIPTION

Figure 1:
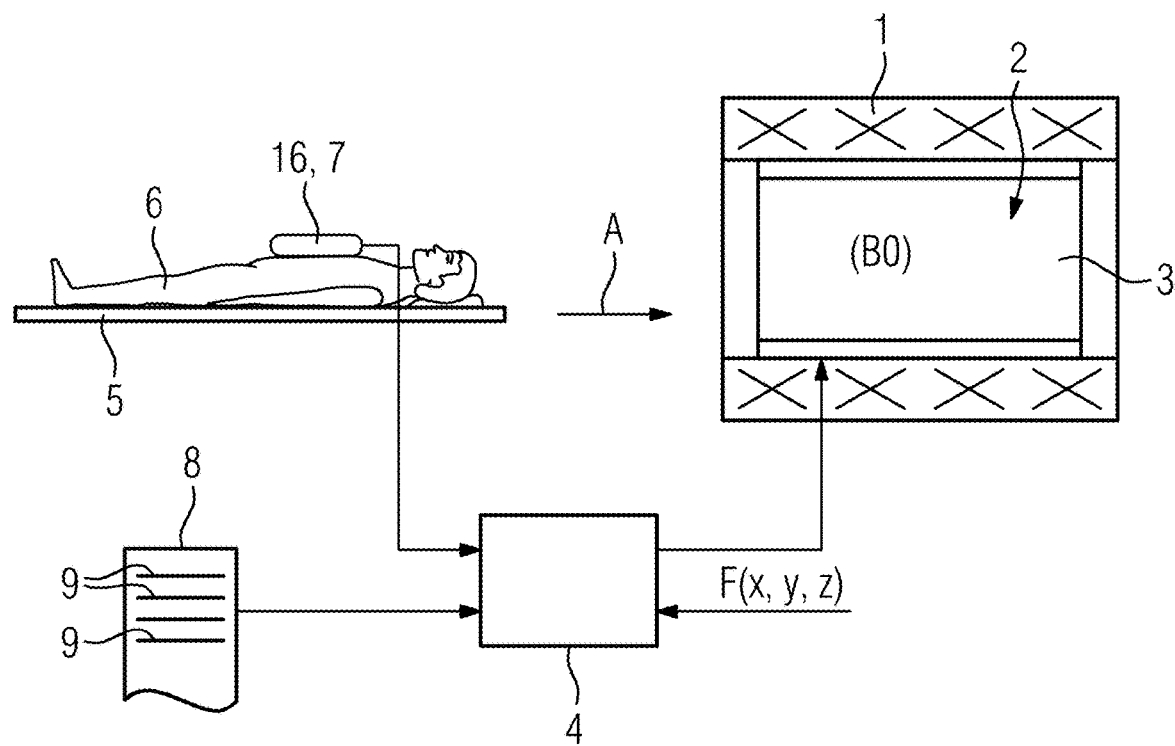
FIG. 1 shows one embodiment of a magnetic resonance system.

According to FIG. 1, one embodiment of a magnetic resonance system includes a main magnet 1. The main magnet 1 generates a main magnetic field B0 in an examination zone 2 of the magnetic resonance system. The examination zone 2 is often embodied as a tunnel. The main magnetic field B0 is static with respect to time and substantially homogeneous with respect to space. A gradient system is generally present in addition. The gradient system is of secondary importance within the scope of the present embodiments and consequently is not shown in FIG. 1 (and also not in the other figures).

The magnetic resonance system also includes a radiofrequency transmit coil 3, hereinafter referred to simply as transmit coil 3. The transmit coil 3 may be embodied as a whole-body coil. The transmit coil 3, however, may also be embodied as a local coil (e.g., a head coil). Using the transmit coil 3, it radiofrequency transmit pulses (e.g., transmit pulses) may be applied to the examination zone 2 or at least to a relevant part of the examination zone 2. The transmit pulse is therefore the pulse emitted into the examination zone 2 in each case by the transmit coil 3. The transmit coil 3 is driven by a control device 4.

The magnetic resonance system also includes a patient couch 5. A patient 6 is arranged on the patient couch 5. The patient 6 or a relevant part of the patient 6 is then introduced into the examination zone 2 by appropriate maneuvering of the patient couch 5. The action of introducing the patient 6 into the examination zone 2 is indicated by an arrow A in FIG. 1. This may alternatively be accomplished manually or under the control of the control device 4.

As a result of the transmit pulses, the patient 6 is excited into emitting magnetic resonance signals. The magnetic resonance signals are received by a radiofrequency receive coil 7 (e.g., a receive coil 7). The receive coil 7 may be identical to the transmit coil 3. In one embodiment, the receive coil 7 is the whole-body coil of the magnetic resonance system. Generally, however, the receive coil 7 is a local coil.

The control device 4 is programmed with a computer program 8. The computer program 8 includes machine code 9 that may be processed by the control device 4. The programming of the control device 4 (e.g., the processing of the machine code 9 by the control device 4) causes the control device 4 to operate the magnetic resonance system in accordance with an operating method that is explained in more detail below in conjunction with FIG. 2.

Figure 2:
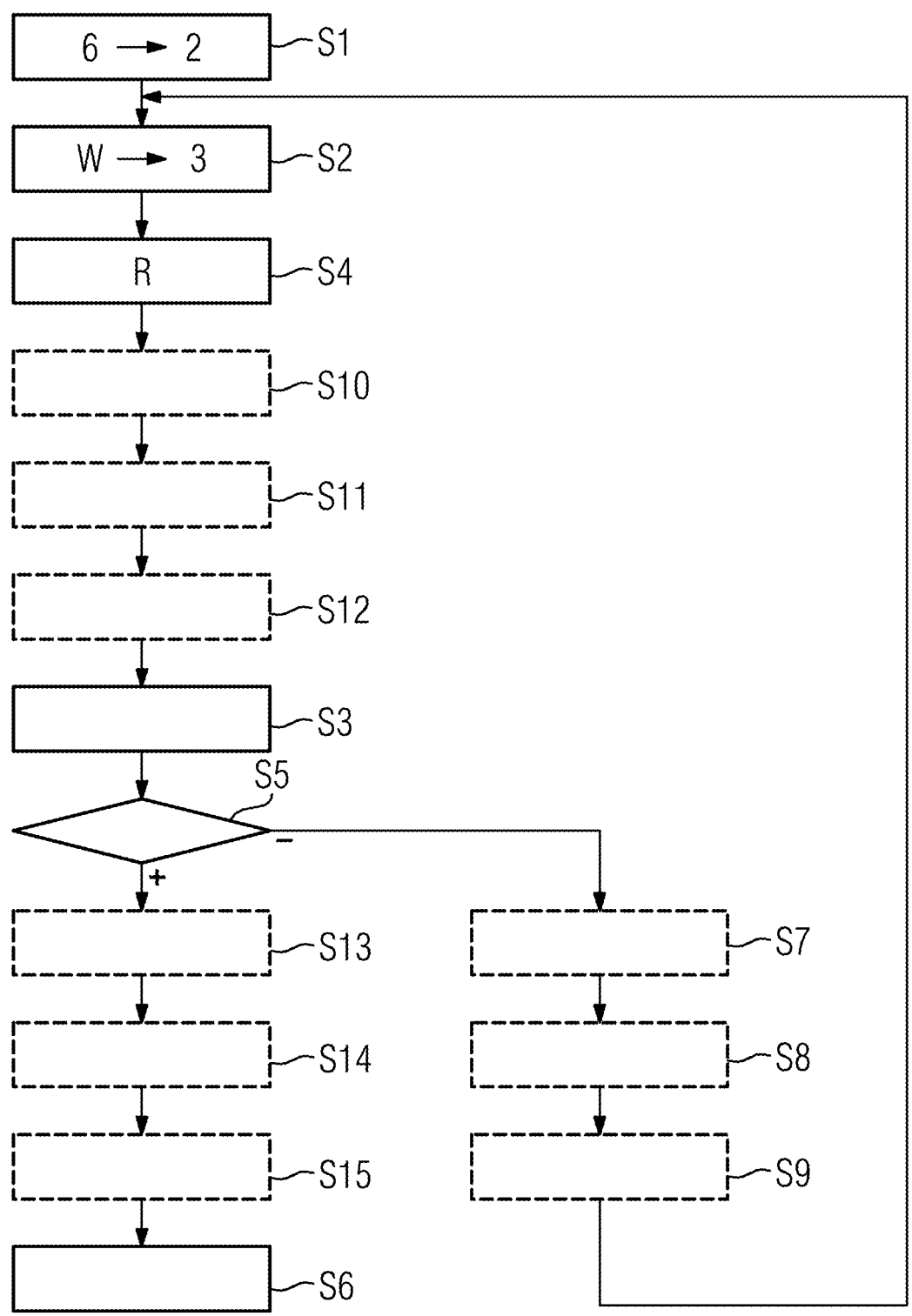
FIG. 2 shows a flowchart of one embodiment of a method.

According to FIG. 2, the patient 6 is first positioned in the examination zone 2 in act S1. As already mentioned, act S1 may be performed by the control device 4 or manually.

Figure 3:
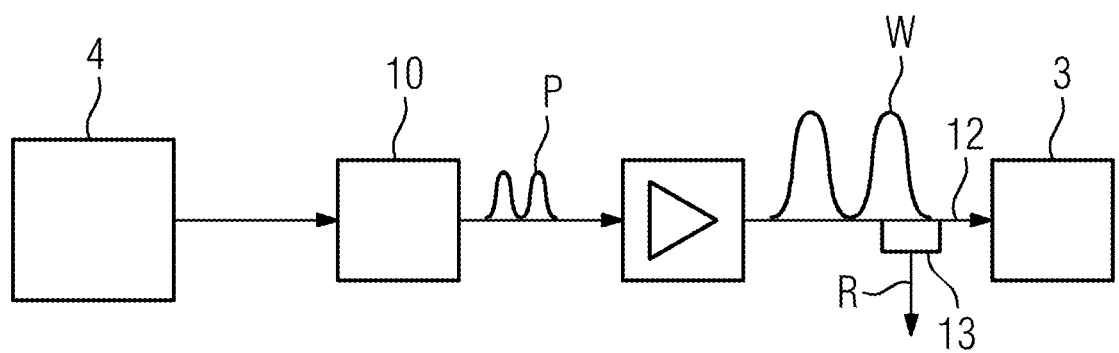
FIG. 3 shows an exemplary transmit path.

In act S2, the control device 4 supplies a radiofrequency wave W to the transmit coil 3. The radiofrequency wave W is referred to below simply as wave W. For example, the control device 4 may drive a pulse generator 10 according to the schematic shown in FIG. 3, such that the pulse generator 10 outputs a corresponding signal pulse P to a power amplifier 11. The power amplifier 11 amplifies the signal pulse P supplied to the power amplifier 11 into the wave W and supplies the wave W to the transmit coil 3 via a line 12. The transmit coil 3 accordingly applies the corresponding transmit pulse to the patient 6. The emitted transmit pulse causes the patient 6 to be excited into emitting magnetic resonance signals. The emitted magnetic resonance signals are received by the receive coil 7 and supplied to the control device 4, which receives and stores the emitted magnetic resonance signals in act S3.

The wave W is not accepted in its entirety by the transmit coil 3 and emitted as a transmit pulse. Rather, a certain portion R of the wave W is reflected back by the transmit coil 3 into the line 12. Within the scope of the present embodiments, the reflected portion R is acquired by the control device 4 in act S4 that precedes act S3. According to the schematic shown in FIG. 3, the reflected portion R is acquired by a first sensor device 13. The first sensor device 13 may be embodied, for example, as a directional coupler 5 that is arranged in the line 12.

In act S5, the control device 4 checks whether the examination of the patient 6 is finished. If this is not the case, the control device 4 returns to act S2, in which the control device 4 applies the next transmit pulse to the patient 6. Otherwise, in act S6, the control device 4 carries out an evaluation of the stored magnetic resonance signals.

During the examination of the patient 6, the patient 6 continues breathing. The main magnetic field B0 changes due to the respiratory motion. The periodicity of the respiratory motion also causes the main magnetic field B0 to change periodically. This phenomenon is well-known to persons skilled in the art. The change in the main magnetic field B0 has an effect on the Larmor frequency because the Larmor frequency is linked to the main magnetic field B0 via the gyromagnetic ratio.

Figure 4:
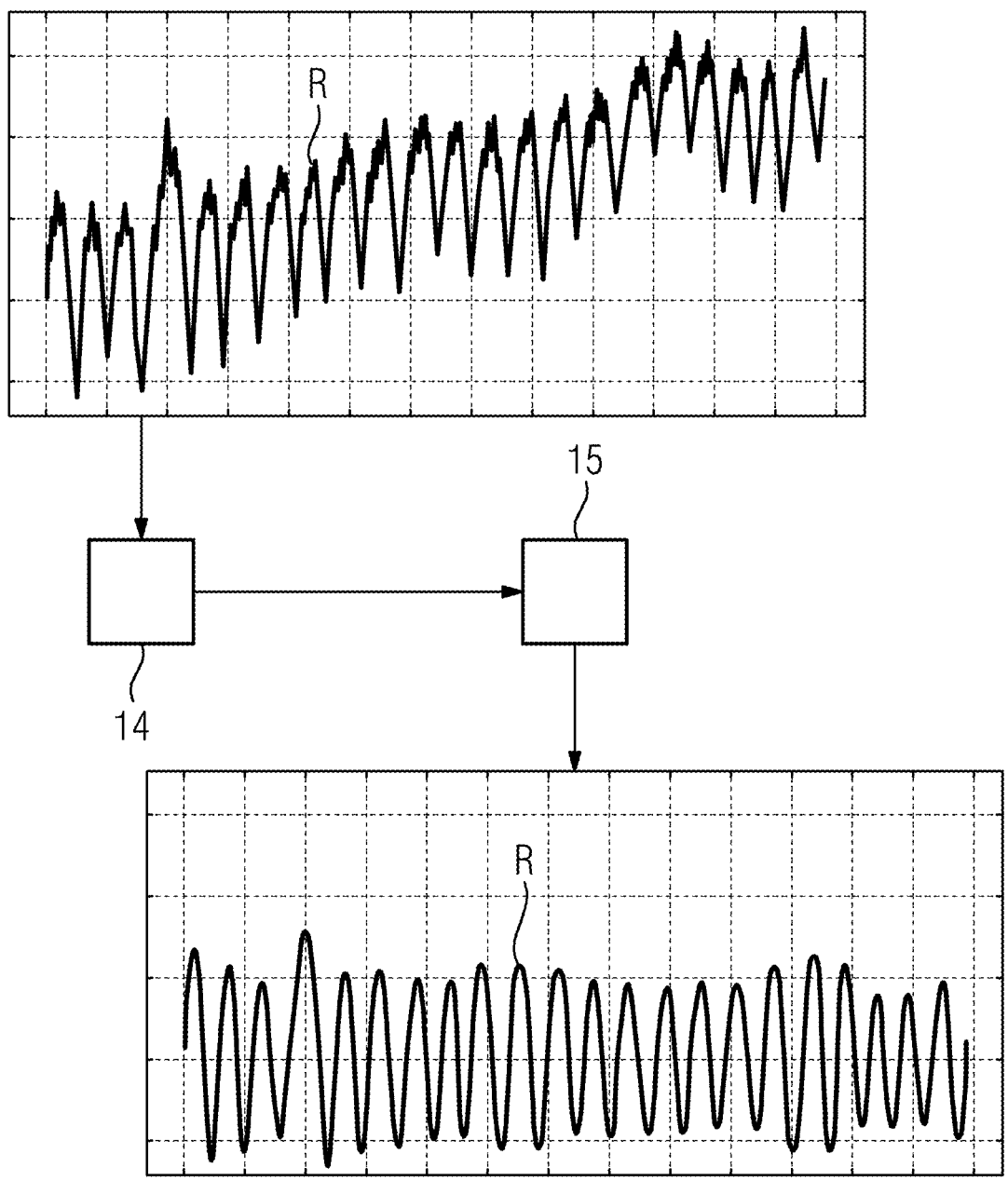
FIG. 4 shows an exemplary oscillation extraction.

The respiratory motion affects not only the main magnetic field B0, but also the reflected portion R. In an upper section, FIG. 4 shows purely by way of example a typical waveform of the reflected portion R during the examination. The reflected portion R changes with the respiratory motion of the patient 6. This oscillating portion is caused by the respiratory motion of the patient 6. The oscillating change is overlaid in addition by a certain relatively high-frequency noise and a drift. The drift is generally caused substantially by thermal effects. The high-frequency noise is unavoidable. The term "high-frequency", in relation to the noise, refers to frequencies that, though considerably greater than the respiratory rate of the patient 6, are usually nonetheless considerably lower than the frequency of the radiofrequency transmit pulses.

Separating the oscillating change and the drift from each other is possible without difficulty. For example, according to the schematic shown in FIG. 4, a corresponding frequency filter 14 may that filters out the drift may be present so that only the oscillating change remains at the output of the frequency filter 14. Removing the noise is also possible without problem. For example, a smoothing function may be performed in an upstream or downstream smoothing element 15 so that a rectified oscillation remains at the output of the smoothing element 15. This is shown purely by way of example in the lower section of FIG. 4. The current end of the established oscillation corresponds to the current elongation of the extracted oscillation.

Various measures are possible in order to compensate for the effect induced by the change in the main magnetic field B0. The measures are explained below in conjunction with FIG. 2. Usually, only one of the below-explained measures will be adopted. The corresponding acts are indicated by a dashed outline in FIG. 2. In principle, however, the measures may also be combined with one another.

Thus, the control device 4 may, for example, perform acts S7 to S9 before repeating act S2. In act S7, as explained hereinabove in conjunction with FIG. 4, the control device 4 extracts the oscillation corresponding to the respiratory motion of the patient 6 from the reflected portions R of previous waves W and, in addition, also establishes the current elongation of the oscillation. In act S8, the control device 4 establishes the currently expected change in the main magnetic field B0 based on the current elongation of the oscillation in conjunction with a function F known to the control device 4. The function F therefore places the expected change in the main magnetic field B0 in relation to the current elongation of the oscillation.

In act S9, the control device 4 correctively adjusts the main magnetic field B0 based on the established expected change in the main magnetic field B0. For example, the control device 4 may energize shim magnets (not shown in the figures) accordingly in act S9. Alternatively or in addition, the control device 4 may correctively adjust the transmit frequency in act S9 for the next transmit pulse.

It is also possible to compensate for the change in the main magnetic field B0 by performing acts S10 to S12. Acts S10 to S12 are arranged between acts S4 and S3. Acts S10 and S11 correspond 1:1 to acts S7 and S8. In act S12, the control device 4 correctively adjusts a nominal receive frequency of the receive coil 7 based on the established expected change in the main magnetic field B0.

In one embodiment, acts S13 to S15 may be performed in order to compensate for the change in the main magnetic field B0. Acts S13 to S15 are arranged between acts S5 and S6. Acts S13 and S14 correspond—just like acts S10 and S11—1:1 to acts S7 and S8. In act S15, the control device 4 brings the acquired and stored magnetic resonance signals into alignment. The result produced by this approach is that the expected change in the main magnetic field B0 is taken into account in the evaluation of the received magnetic resonance signals. In this case (e.g., taking the change into account within the scope of the subsequent evaluation of the magnetic resonance signals), the respective reflected portion R is to be assigned to the magnetic resonance signals within the scope of act S3.

The above-explained ways of taking the change in the main magnetic field B0 into account are known per se. There is, therefore, no need to explain these ways in any further detail. The known methods, however, are not based on the determining of the change in the main magnetic field B0 based on the extracted oscillation of the reflected portion R, but on other methods (e.g., based on a direct measurement of the change in the main magnetic field B0). Generally, the last-mentioned variant is to be preferred (e.g., taking the change in the main magnetic field B0 into account only during the evaluation). This is because this variant may be carried out with a higher degree of precision than the other two variants.

Within the scope of the above explanations of the present embodiments, act S4 is performed for all transmit pulses. However, it is often sufficient to perform act S4 only for some of the transmit pulses (e.g., for every third or every fifth transmit pulse).

In the simplest case, the function F of the control device 4 is known in advance. The formulation "known in advance" provides, in this context, that the function F of the control device 4 is already known prior to the execution of act S1 (e.g., before the patient 6 is arranged in the examination zone 2). In this case, the relationship between the elongation of the extracted oscillation and the change in the main magnetic field B0 may have been established, for example, within the scope of previously performed test measurements and stored as function F in the control device 4. Alternatively, the function F may be determined only after the patient 6 has been arranged in the examination zone 2. This is explained in more detail below in conjunction with FIG. 5.

Figure 5:
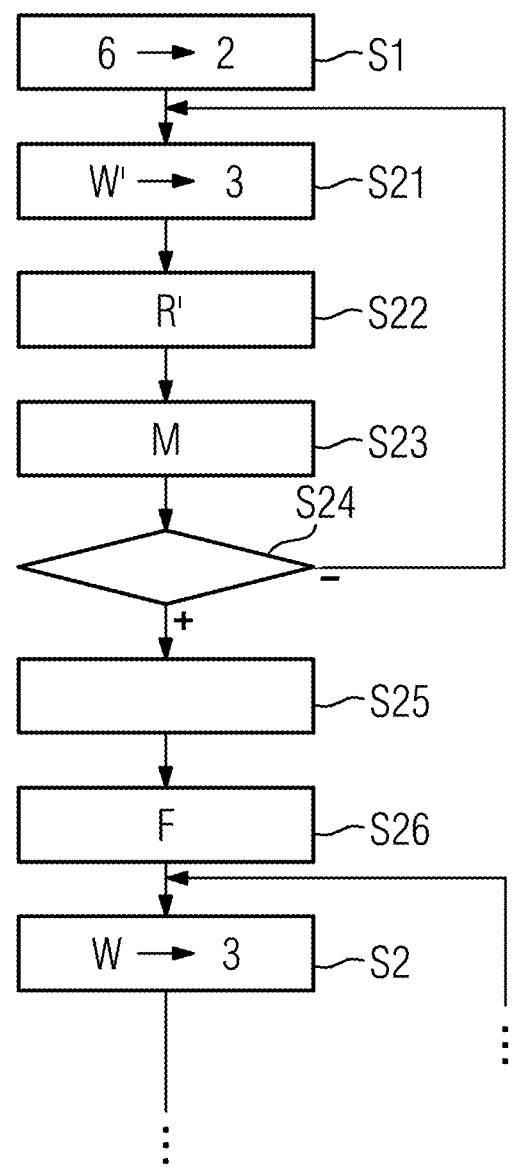
FIG. 5 shows a flowchart of one embodiment of a method.

According to FIG. 5, just as in FIG. 2, the patient 6 is first arranged in the examination zone 2 in act S1. However, acts S21 to S26 are performed before act S2 and acts S3 to S15 following act S2 are performed for the first time.

In act S21, the control device 4 supplies a radiofrequency wave W' to the transmit coil 3. This causes the control device 4 to apply a radiofrequency sample pulse (e.g., a sample pulse) to the transmit coil 3. Act S21 corresponds in terms of content to act S2. The transmit coil 3 applies the sample pulse to the patient 6 by this. The sample pulse may be a phase scout, for example.

Phase scouts are known to persons skilled in the art. Phase scouts consist of rapidly repeated measurements by of which the variation with time of the phase change $\Delta\varphi$ is determined in a specific region of the patient 6. In MR scanners of the Applicant, for example, this method is known by the name "PACE".

In act S22, the reflected portion R' of the wave W' is acquired by the first sensor device 13. Act S22 corresponds in terms of content to act S4. In addition, in act S23, a measured variable M that is characteristic of the change in the main magnetic field B0 during the respective sample pulse is acquired by a second sensor device 16. The type of measured variable M may be as requirements dictate. The measured variable M is different than the reflected portion R'. For example, an echo produced by the phase scout may be captured by the receive coil 7.

In act S24, the control device 4 thereupon checks whether the test measurements have already been completed. If this is not the case, the control device 4 returns to act S21, in which the control device 4 outputs the next sample pulse. Otherwise, the control device transitions to act S25. In act S25, the control device 4 establishes, based on the measured variable M, the change in the main magnetic field B0 during the sample pulses. In act S25, the control device 4 may, for example, determine a phase shift $\Delta\varphi$ in conjunction with the echo time TE of the echo captured in act S23. In this case, the control device 4 may initially determine the shift in the Larmor frequency based on the relationship $\Delta f = \Delta\varphi/(360°*TE)$ and from this, establishes the change in the main magnetic field B0 based on the gyromagnetic ratio. The corresponding procedure is known to persons skilled in the art.

Thus, both the oscillation of the reflected portion R' induced by the respiratory motion and the associated changes in the main magnetic field B0 are now known to the control device 4. The control device 4 may therefore determine the function F in act S26. For example, the peak values of the frequency change $\Delta f$ may be placed in relation to the peak values of the oscillation extracted from the reflected portions R', and in this way, a ratio factor may be determined. If necessary, filtering operations may be performed within the scope of the determination.

In principle, the approach explained above in conjunction with FIG. 5 may also be applied for predetermining the function F. In this case, acts S1 and S21 to S25 are performed for a plurality of test subjects, and the results thereupon are evaluated collectively in act S26. The result of the evaluation yields the function F.

In the simplest case, the function F is a simple scalar that applies to the whole of the examination zone 2. However, the function F, at least within the examination zone 2, may be specified in a spatially resolved manner. This is indicated in FIG. 1 by the function F additionally being provided with coordinates x, y, z. In this case, the control device 4 may also establish the expected change in the main magnetic field B0 within the examination zone 2 in a spatially resolved manner.

To sum up, the present embodiments therefore relate to the following situation.

In an examination zone 2 of an MR system, a main magnet 1 of the MR system generates a main magnetic field B0 that is static with respect to time and substantially homogeneous with respect to space. In order to excite a patient 6 into emitting MR signals, a control device 4 of the MR system supplies a plurality of radiofrequency waves W to an RF transmit coil 3. The RF transmit coil 3 applies corresponding RF transmit pulses to the patient 6. An RF receive coil 7 receives the excited MR signals and supplies the excited MR signals to the control device 4, which evaluates the excited MR signals. In order to compensate for the effect of a change in the main magnetic field B0 varying with a respiratory motion of the patient 6, the control device 4 establishes a change in the main magnetic field B0 expected for a respective time instant and, based on the established expected change in the main magnetic field B0, correctively adjusts the main magnetic field B0 and/or a nominal receive frequency of the RF receive coil 7 and/or a transmit frequency for subsequent RF transmit pulses and/or takes the expected change in the main magnetic field B0 into account in the evaluation of the received MR signals. At least for some of the RF transmit pulses, the control device 4 acquires, via a sensor device 13, a portion R of the respective radiofrequency wave W supplied to the RF transmit coil 3. The portion R is reflected by the RF transmit antenna 3. The control device extracts therefrom an oscillation corresponding to a respiratory motion of the patient 6 and, based on the variation with time of the extracted oscillation, establishes the change in the main magnetic field B0 expected for the respective time instant.

The present embodiments have many advantages. For example, the change in the main magnetic field B0 may be established without any requirement for additional hardware and without any need to change an acquisition scheme in the case of an imaging measurement.

Although the invention has been illustrated and described in greater detail based on the exemplary embodiments, the invention is not limited by the disclosed examples. Other variations may be derived herefrom by the person skilled in the art without leaving the scope of protection of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. An operating method for a magnetic resonance system comprising a main magnet configured to generate a main magnetic field that is static with respect to time and substantially homogeneous with respect to space in an examination zone of the magnetic resonance system, the operating method comprising:

exciting a patient located in the examination zone into emitting magnetic resonance signals, wherein the exciting of the patient comprises supplying, by a controller of the magnetic resonance system, a plurality of radiofrequency waves to a radiofrequency transmit coil, such that the radiofrequency transmit coil applies radiofrequency transmit pulses to the patient;

receiving, by a radiofrequency receive coil, the magnetic resonance signals emitted by the patient and supplying the magnetic resonance signals received by the radiofrequency receive coil to the controller;

evaluating, by the controller, the magnetic resonance signals supplied to the controller;

compensating for an effect of a change in the main magnetic field varying with a respiratory motion of the patient, wherein the compensating for the effect of the change in the main magnetic field comprises establishing, by the controller, a change in the main magnetic field expected for a respective time instant and, based on the change in the main magnetic field expected for the respective time instant, correctively adjusting the main magnetic field, correctively adjusting a nominal receive frequency of the radiofrequency receive coil, correctively adjusting a transmit frequency for subsequent radiofrequency transmit pulses, taking the change expected for the respective time instant in the main magnetic field into account in evaluating the magnetic resonance signals supplied to the controller, or any combination thereof;

acquiring, by the controller, via a sensor device, a portion of a respective radiofrequency wave of the plurality of radiofrequency waves supplied to the radiofrequency transmit coil for at least some of the radiofrequency transmit pulses, the portion of the respective radiofrequency wave being reflected by the radiofrequency transmit coil; and extracting, by the controller, an oscillation corresponding to the respiratory motion of the patient from the portions of the respective radiofrequency waves reflected by the radiofrequency transmit coil, wherein establishing the change in the main magnetic field expected for the respective time instant comprises establishing, by the controller, the change in the main magnetic field expected for the respective time instant based on a variation with time of the oscillation corresponding to the respiratory motion of the patient.

2. The operating method of claim 1, wherein establishing the change in the main magnetic field expected for the respective time instant comprises establishing, by the controller, the change expected for the respective time instant in the main magnetic field based on the variation with time of the oscillation corresponding to the respiratory motion of the patient in conjunction with a function already predefined before the patient is arranged in the examination zone, the function placing the change expected for the respective time instant in the main magnetic field in relation to a current elongation of the oscillation.

3. The operating method of claim 1, further comprising initially performing, by the controller, test measurements once the patient has been arranged in the examination zone, wherein initially performing the test measurements comprises:

supplying a radiofrequency wave to the radiofrequency transmit coil in each case, such that a radiofrequency sample pulse is applied to the radiofrequency transmit coil in each case;

acquiring in each case during the radiofrequency sample pulses, via the sensor device, a portion of the respective radiofrequency wave supplied to the radiofrequency transmit coil, the portion of the respective radiofrequency wave being reflected by the radiofrequency transmit coil;

additionally acquiring, via a further sensor device, a measured variable that is different from the portion reflected by the radiofrequency transmit coil and is characteristic of the change in the main magnetic field during the radiofrequency sample pulses;

establishing, by the controller, the change in the main magnetic field during the radiofrequency sample pulses based on the measured variable that is different from the portion reflected by the radiofrequency transmit coil;

determining, by the controller, a function that places the change expected for the respective time instant in the main magnetic field in relation to a current elongation of the oscillation based on the portions reflected by the radiofrequency transmit coil during the radiofrequency sample pulses and the change in the main magnetic field; and establishing, by the controller, the change expected for the respective time instant in the main magnetic field based on the variation with time of the oscillation in conjunction with the function determined by the controller.

4. The operating method of claim 1, wherein establishing the change in the main magnetic field expected for the respective time instant comprises establishing, by the controller, the change expected for the respective time instant in the main magnetic field within the examination zone in a spatially resolved manner.

5. In a non-transitory computer-readable storage medium that stores instructions executable by a controller of a magnetic resonance system to operate the magnetic resonance system, the magnetic resonance system comprising a main magnet configured to generate a main magnetic field that is static with respect to time and substantially homogeneous with respect to space in an examination zone of the magnetic resonance system, the instructions comprising:

exciting a patient located in the examination zone into emitting magnetic resonance signals, wherein the exciting of the patient comprises supplying, by a controller of the magnetic resonance system, a plurality of radiofrequency waves to a radiofrequency transmit coil, such that the radiofrequency transmit coil applies radiofrequency transmit pulses to the patient;

receiving, by a radiofrequency receive coil, the magnetic resonance signals and supplying the magnetic resonance signals received by the radiofrequency receive coil to the controller;

evaluating, by the controller, the magnetic resonance signals supplied to the controller;

compensating for an effect of a change in the main magnetic field varying with a respiratory motion of the patient, wherein the compensating for the effect of the change in the main magnetic field comprises establishing, by the controller, a change in the main magnetic field expected for a respective time instant and based on the change expected for the respective time instant in the main magnetic field, correctively adjusting the main magnetic field, correctively adjusting a nominal receive frequency of the radiofrequency receive coil, correctively adjusting a transmit frequency for subsequent radiofrequency transmit pulses, taking the change expected for the respective time instant in the main magnetic field into account in evaluating the magnetic resonance signals supplied to the controller, or any combination thereof;

acquiring, by the controller, via a sensor device, a portion of a respective radiofrequency wave of the plurality of radiofrequency waves supplied to the radiofrequency transmit coil for at least some of the radiofrequency transmit pulses, the portion of the respective radiofrequency wave being reflected by the radiofrequency transmit coil; and extracting, by the controller, an oscillation corresponding to the respiratory motion of the patient from the portions of the respective radiofrequency waves reflected by the radiofrequency transmit coil, wherein establishing the change in the main magnetic field expected for the respective time instant comprises establishing, by the controller, the change in the main magnetic field expected for the respective time instant based on a variation with time of the oscillation corresponding to the respiratory motion of the patient.

6. The non-transitory computer-readable storage medium of claim 5, wherein establishing the change in the main magnetic field expected for the respective time instant comprises establishing, by the controller, the change expected for the respective time instant in the main magnetic field based on the variation with time of the oscillation corresponding to the respiratory motion of the patient in conjunction with a function already predefined before the patient is arranged in the examination zone, the function placing the change expected for the respective time instant in the main magnetic field in relation to a current elongation of the oscillation.

7. The non-transitory computer-readable storage medium of claim 5, wherein the instructions further comprise initially performing, by the controller, test measurements once the patient has been arranged in the examination zone, wherein the initially performing the test measurements comprises:

supplying a radiofrequency wave to the radiofrequency transmit coil in each case, such that a radiofrequency sample pulse is applied to the radiofrequency transmit coil in each case;

acquiring in each case during the radiofrequency sample pulses, via the sensor device, a portion of the respective radiofrequency wave supplied to the radiofrequency transmit coil, the portion of the respective radiofrequency wave being reflected by the radiofrequency transmit coil;

additionally acquiring, via a further sensor device, a measured variable that is different from the portion reflected by the radiofrequency transmit coil and is characteristic of the change in the main magnetic field during the radiofrequency sample pulses;

establishing, by the controller, the change in the main magnetic field during the radiofrequency sample pulses based on the measured variable that is different from the portion reflected by the radiofrequency transmit coil;

determining, by the controller, a function that places the change expected for the respective time instant in the main magnetic field in relation to a current elongation of the oscillation based on the portions reflected by the radiofrequency transmit coil during the radiofrequency sample pulses and the change in the main magnetic field; and establishing, by the controller, the change expected for the respective time instant in the main magnetic field based on the variation with time of the oscillation in conjunction with the function determined by the controller.

8. The non-transitory computer-readable storage medium of claim 5, wherein establishing the change in the main magnetic field expected for the respective time instant comprises establishing, by the controller, the change expected for the respective time instant in the main magnetic field within the examination zone in a spatially resolved manner.

9. A controller for a magnetic resonance system configured to operate the magnetic resonance system, the magnetic resonance system comprising a main magnet configured to generate a main magnetic field that is static with respect to time and substantially homogeneous with respect to space in an examination zone of the magnetic resonance system, the controller comprising:

a processor configured to:
excite a patient located in the examination zone into emitting magnetic resonance signals, wherein excitation of the patient comprises supply of a plurality of radiofrequency waves to a radiofrequency transmit coil, such that the radiofrequency transmit coil applies radiofrequency transmit pulses to the patient, the magnetic resonance signals being receivable by a radiofrequency receive coil and being suppliable to the processor;

evaluate the magnetic resonance signals supplied to the controller;

compensate for an effect of a change in the main magnetic field varying with a respiratory motion of the patient, wherein compensation for the effect of the change in the main magnetic field comprises establishment of a change in the main magnetic field expected for a respective time instant and based on the change expected for the respective time instant in the main magnetic field, corrective adjustment of the main magnetic field, corrective adjustment of a nominal receive frequency of the radiofrequency receive coil, corrective adjustment of a transmit frequency for subsequent radiofrequency transmit pulses, take the change expected for the respective time instant in the main magnetic field into account in evaluating the magnetic resonance signals supplied to the controller, or any combination thereof;

acquire, via a sensor device, a portion of a respective radiofrequency wave of the plurality of radiofrequency waves supplied to the radiofrequency transmit coil for at least some of the radiofrequency transmit pulses, the portion of the respective radiofrequency wave being reflected by the radiofrequency transmit coil; and extract an oscillation corresponding to the respiratory motion of the patient from the portions of the respective radiofrequency waves reflected by the radiofrequency transmit coil, wherein establishment of the change in the main magnetic field expected for the respective time instant comprises establishment of the change in the main magnetic field expected for the respective time instant based on a variation with time of the oscillation corresponding to the respiratory motion of the patient.

10. A magnetic resonance system comprising:
a main magnet configured to generate a main magnetic field that is static with respect to time and substantially homogeneous with respect to space in an examination zone of the magnetic resonance system;

a radiofrequency transmit coil configured to apply a plurality of radiofrequency transmit pulses to the examination zone, such that a patient located in the examination zone is excited into emitting magnetic resonance signals;

a radiofrequency receive coil configured to receive magnetic resonance signals emitted by the patient following excitation of the patient;

a sensor device configured to acquire, at least for some of the radiofrequency transmit pulses, a portion of the respective radiofrequency wave supplied to the radiofrequency transmit coil, the portion of the respective radiofrequency wave being reflected by the radiofrequency transmit coil; and a controller configured to:
  evaluate the magnetic resonance signals;
  compensate for an effect of a change in the main magnetic field varying with a respiratory motion of the patient, wherein compensation for the effect of the change in the main magnetic field comprises establishment of a change in the main magnetic field expected for a respective time instant and based on the change expected for the respective time instant in the main magnetic field, corrective adjustment of the main magnetic field, corrective adjustment of a nominal receive frequency of the radiofrequency receive coil, corrective adjustment of a transmit frequency for subsequent radiofrequency transmit pulses, take the change expected for the respective time instant in the main magnetic field into account in evaluating the magnetic resonance signals supplied to the controller, or any combination thereof; and
  extract an oscillation corresponding to the respiratory motion of the patient from the portions of the respective radiofrequency waves reflected by the radiofrequency transmit coil, wherein the establishment of the change in the main magnetic field expected for the respective time instant comprises establishment of the change in the main magnetic field expected for the respective time instant based on a variation with time of the oscillation corresponding to the respiratory motion of the patient.

* * * * *